(12) United States Patent
Hercouet et al.

(10) Patent No.: US 7,988,737 B2
(45) Date of Patent: Aug. 2, 2011

(54) READY-TO-USE COMPOSITION FOR OXIDATION DYEING OF KERATIN FIBERS COMPRISING AT LEAST ONE FATTY SUBSTANCE CHOSEN FROM FATTY AMIDES AND FATTY ACID ESTERS, AT LEAST ONE DYE PRECURSOR, AT LEAST ONE OXIDIZING AGENT AND OPTIONALLY AT LEAST ONE ALKALINE AGENT, AND METHODS AND KITS THEREWITH

(75) Inventors: Leïla Hercouet, Neuilly Plaisance (FR); Frédéric Simonet, Clichy (FR); Franck Clement, Sainte Genevieve des Bois (FR); Marie-Pascale Audousset, Asnieres (FR); Isabelle Schlosser, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,492

(22) Filed: Dec. 18, 2009

(65) Prior Publication Data

US 2010/0162492 A1 Jul. 1, 2010

Related U.S. Application Data

(60) Provisional application No. 61/150,096, filed on Feb. 5, 2009.

(30) Foreign Application Priority Data

Dec. 19, 2008 (FR) ...................................... 08 07288

(51) Int. Cl.
*A61Q 5/10* (2006.01)
(52) U.S. Cl. ............. 8/405; 8/406; 8/410; 8/411; 8/421; 8/435; 8/580; 8/604; 8/619
(58) Field of Classification Search .............. 8/405, 406, 8/410, 411, 421, 435, 580, 604, 619
See application file for complete search history.

(56) References Cited

U.S. PATENT DOCUMENTS

| | | |
|---|---|---|
| 3,100,739 A | 8/1963 | Kaiser et al. |
| 3,369,970 A | 2/1968 | McLaughlin et at |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,826,681 A | 5/1989 | Jacquet et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 * | 6/2001 | Laurent et al. ............... 424/70.1 |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |

(Continued)

FOREIGN PATENT DOCUMENTS

CA 1 268 421 5/1990

(Continued)

OTHER PUBLICATIONS

STIC Search Report dated Jul. 14, 2010.*
French Search Report for FR 0807288, dated Nov. 4, 2009.
English language abstract of FR 2 870 724 A1, Dec. 2, 2005.
English language abstract of JP 1-165514, Jun. 29, 1989.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.

(Continued)

*Primary Examiner* — Eisa B Elhilo
(74) *Attorney, Agent, or Firm* — Finnegan, Henderson, Farabow, Garrett & Dunner, LLP

(57) ABSTRACT

Provided is a ready-to-use composition for the oxidation dyeing of keratin fibers, and for example of human keratin fibers such as the hair, comprising: A) at least one fatty substance present in an amount of greater than or equal to 25% by weight relative to the total weight of the ready-to-use composition, at least one of the at least one fatty substance being chosen from fatty amides and fatty acid esters, B) at least one dye precursor, C) at least one oxidizing agent and optionally D) at least one alkaline agent. Also provided is a method of dyeing of keratin fibres, comprising applying a ready-to-use composition to the keratin fibres for a sufficient time to develop the desired coloration.

23 Claims, No Drawings

U.S. PATENT DOCUMENTS

| | | | |
|---|---|---|---|
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | LeGrand |
| 7,651,533 B2 | 1/2010 | LeGrand |
| 7,651,536 B2 | 1/2010 | Cottard et al. |
| 7,740,663 B2 | 6/2010 | De La Mettrie et al. |
| 7,766,977 B2 | 8/2010 | Cottard et al. |
| 7,799,095 B2 | 9/2010 | Mario et al. |
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | Legrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1* | 11/2006 | Legrand ............................ 8/405 |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 B1 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 A1 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 449 512 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 B1 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 A1 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 A | 1/1985 |
| GB | 2 170 830 | 8/1986 |
| GB | 2 188 948 A | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |

| | | |
|---|---|---|
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 A1 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,093, filed Dec. 22, 2010.
Copending U.S. Appl. No. 12/976,124, filed Dec. 22, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of De 199 62 869, dated Jun. 28, 2001.
English language Abstract of De 38 14 356, dated Sep. 8, 1988.
English language Abstract of De 43 09 509, dated Sep. 19, 1994.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010,.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.

French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 3, 2010, in co-pending U.S. Appl. No. 12/642,451.
STIC Search Report for U.S. Appl. No. 12/339,820, dated Jan. 21, 2010.

* cited by examiner

READY-TO-USE COMPOSITION FOR OXIDATION DYEING OF KERATIN FIBERS COMPRISING AT LEAST ONE FATTY SUBSTANCE CHOSEN FROM FATTY AMIDES AND FATTY ACID ESTERS, AT LEAST ONE DYE PRECURSOR, AT LEAST ONE OXIDIZING AGENT AND OPTIONALLY AT LEAST ONE ALKALINE AGENT, AND METHODS AND KITS THEREWITH

This application claims benefit of U.S. Provisional Application No. 61/150,096, filed Feb. 5, 2009. This application also claims benefit of priority under 35 U.S.C. §119 to French Patent Application No. 0807288, filed Dec. 19, 2008.

Disclosed herein is a ready-to-use composition for the oxidation dyeing of keratin fibers.

Dyeing of keratin fibers and for example human hair with dyeing compositions containing oxidation dyes, such as precursors of oxidation dyes and color modifiers, is known.

The precursors of oxidation dyes, generally called oxidation bases, may be initially compounds that are colorless or faintly colored which, when combined with oxidizing products, can give rise by a process of oxidative condensation to colored and coloring compounds. These generally can be compounds such as ortho- or para-phenylenediamines, ortho- or para-aminophenols and heterocyclic bases.

It may be also known that the shades obtained with these oxidation bases can be varied by combining them with couplers or color modifiers, the latter generally being chosen from meta-diaminobenzenes, meta-aminophenols, meta-diphenols and certain heterocyclic compounds such as indole compounds.

The variety of the molecules employed as oxidation bases and couplers means that a rich palette of colors can be obtained.

The so-called "permanent" coloring obtained with these oxidation dyes, also called oxidation coloring, should moreover satisfy at least one of a certain number of requirements. Thus, it should be harmless from the toxicological standpoint, it should permit shades to be obtained with the desired intensity and should be durable under the action of external aggressive factors such as light, weather, washing, perming, sweat and/or rubbing.

The dyes should also be able to cover white hair, and finally should have the least possible selectivity, i.e. must give the smallest possible differences in coloration along one and the same keratin fiber, which may generally comprises zones that can be sensitized (i.e. damaged) to a varying extent from its tip to its root.

There have been numerous attempts in the area of hair coloring to improve dyeing properties, for example via additives. However, selection of these additives can be difficult, since they should improve the dyeing properties of dyeing compositions without having an adverse effect on the other properties of these compositions. For example, these additives should not adversely affect the properties of lightening of keratin fibers and the application properties of the coloring.

Accordingly, one aspect of the present disclosure are novel ready-to-use compositions for the oxidation dyeing of keratin fibers that can avoid at least one of the drawbacks of the prior art. For example, disclosed herein are ready-to-use compositions for oxidation coloring of keratin fibers, displaying improved dyeing properties so that the desired lightening can be achieved, and which can be easy to mix and apply, for example, which do not run and thus remain in place at the point of application. "Improved dyeing properties" means, for example, improvement with respect to the depth/intensity and/or uniformity of dyeing.

Thus, provided herein is a ready-to-use composition for the oxidation dyeing of keratin fibers, and for example of human keratin fibers such as the hair, comprising, A) at least one fatty substance present in an amount of greater than or equal to 25% by weight relative to the total weight of the ready-to-use composition, at least one of the at least one fatty substance being chosen from fatty amides and fatty acid esters, B) at least one dye precursor, C) at least one oxidizing agent, and optionally D) at least one alkaline agent.

The ready-to-use composition according to the present disclosure may have improved dyeing properties. For example, the ready-to-use composition of the disclosure may lead to coloring that has good depth and/or intensity and/or good uniformity of the color along the fiber between the hair tip and root (also called the selectivity of coloring) and/or good chromaticity. The ready-to-use composition of the disclosure can be applied without difficulty on keratin fibers, without running. This ready-to-use composition may also produce less degradation of the keratin fibers during the coloring process.

Finally, the coloring obtained via of the ready-to-use compositions of the disclosure may be durable, and may withstand the various aggressive external factors to which keratin fibers may be subjected.

Provided herein is also a method of dyeing of keratin fibers, comprising applying to the keratin fibers the ready-to-use composition according to the disclosure for a sufficient time to develop the desired coloration.

Further provided is a multi-compartment kit for application of the various components of the ready-to-use composition of the disclosure.

As already mentioned, the ready-to-use composition of the disclosure comprises at least one fatty substance.

As used herein, "fatty substance" are organic compounds that are insoluble in water at normal temperature (25° C.) and at atmospheric pressure (760 mmHg) (solubility below 5% and such as below 1% and further such as below 0.1%). In their structure they have a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

According to at least one embodiment, the ready-to-use composition comprises at least 25% by weight of fatty substances other than fatty acids relative to the total weight of the ready-to-use composition.

Among the fatty substances, the ready-to-use composition of the disclosure can comprise at least one fatty amide of an alkanolamine, optionally substituted, and of a $C_9$-$C_{30}$ fatty acid. The alkanolamine is for example a $C_2$-$C_{10}$, such as $C_2$-$C_4$, mono- or dialkanolamine.

For example, the at least one fatty amide that can be used in the present disclosure can be chosen from compounds of formula (I):

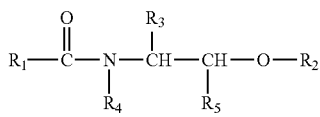
(I)

wherein:
- $R_1$ denotes either a linear or branched, saturated or unsaturated $C_9$-$C_{30}$ hydrocarbon radical, which can be substituted with at least one hydroxyl group, the at least one hydroxyl group being optionally esterified by a saturated or unsaturated $C_{16}$-$C_{30}$ fatty acid; or a radical R''—(NR—CO)—R', where R denotes a hydrogen atom or a mono- or polyhydroxylated, for example monohydroxylated, $C_1$-$C_{10}$ hydrocarbon radical, R' and R'' are hydrocarbon radicals wherein the total number of carbon atoms range from 9 to 30, R' being a divalent radical;
- $R_2$ denotes a hydrogen atom or a (glycosyl)$_n$, (galactosyl)$_m$ or sulphogalactosyl radical, wherein n is an integer ranging from 1 to 4 and m is an integer ranging from 1 to 8;
- $R_3$ denotes a hydrogen atom or a saturated or unsaturated $C_{16}$-$C_{27}$ hydrocarbon radical, which can be substituted with at least one $C_1$-$C_{14}$ alkyl radical; $R_3$ can also denote a $C_{15}$-$C_{26}$ α-hydroxyalkyl radical whose hydroxyl group can optionally be esterified by a $C_{16}$-$C_{30}$ α-hydroxyacid;
- $R_4$ denotes a hydrogen atom, a saturated or unsaturated $C_{16}$-$C_{27}$ hydrocarbon radical, a $C_2$-$C_6$ hydroxyalkyl radical or a radical —CH$_2$—CHOH—CH$_2$—O—$R_6$ wherein $R_6$ denotes a $C_{10}$-$C_{26}$ hydrocarbon radical;
- $R_5$ denotes a hydrogen atom or a mono- or polyhydroxylated $C_1$-$C_4$ hydrocarbon radical.

According to at least one embodiment, the at least one fatty amide is a ceramide, such as a ceramide of formula (I) above in which $R_1$ denotes a saturated or unsaturated alkyl radical derived from $C_{16}$-$C_{22}$ fatty acids, optionally hydroxylated; $R_2$ denotes a hydrogen atom; and $R_3$ denotes a $C_{16}$ α-hydroxyalkyl radical.

As examples of ceramide, mentions can be made of
N-linoleoyldihydrosphingosine,
N-oleoyldihydrosphingosine,
N-palmitoyldihydrosphingosine,
N-stearoyldihydrosphingosine,
N-behenoyldihydrosphingosine,
N-2-hydroxypalmitoyldihydrosphingosine,
N-stearoylphytosphingosine,
or mixtures thereof, and such as N-oleoyldihydrosphingosine, N-2-hydroxypalmitoyldihydrosphingosine and N-stearoylphytosphingosine.

Among the fatty amides usable in the ready-to-use composition of the disclosure, non-limiting mentions can be made of amides of mono- or di-alkanolamine and of $C_{12}$-$C_{30}$, such as $C_{14}$-$C_{30}$ fatty acid, for example of a $C_2$-$C_{10}$, or even $C_2$-$C_6$, alkanolamine and a $C_{14}$-$C_{22}$ fatty acid.

The fatty acid can be saturated or unsaturated, linear or branched.

As examples of amide of an alkanolamine and of a $C_{12}$-$C_{30}$ fatty acid (B), mentions can be made of:
- the diethanolamide of oleic acid, such as the amide marketed under the trade name MEXANYL® GT by the company CHIMEX,
- the monoethanolamide of myristic acid, such as the amide marketed under the trade name COMPERLAN® MM by the company COGNIS,
- the diethanolamide of soya fatty acids, such as the amide marketed under the trade name COMPERLAN® VOD by the company COGNIS,
- the ethanolamide of stearic acid, such as the amide marketed under the trade name MONAMID® S by the company UNIQEMA,
- the monoisopropanolamide of oleic acid, such as the amide marketed under the trade name WITCAMIDE® 61 by the company WITCO,
- the diethanolamide of linoleic acid, such as the amide marketed under the trade name PURTON° SFD by the company ZSCHIMMER SCHWARZ,
- the monoethanolamide of stearic acid, such as the amide marketed under the trade name MONAMID® 972 by the company ICI/UNIQEMA,
- the monoethanolamide of behenic acid, such as the amide marketed under the trade name INCROMIDE® BEM by CRODA,
- the monoisopropanolamide of isostearic acid, such as the amide marketed under the trade name WITCAMIDE® SPA by the company WITCO,
- the diethanolamide of erucic acid, such as the amide marketed under the name diethanolamide of erucic acid by the company STEARINERIES DUBOIS,
- the monoethanolamide of ricinoleic acid, such as the amide marketed under the name ricinoleic monoethanolamide by the company STEARINERIES DUBOIS.
- the monoisopropanolamide of copra acids, such as the amide marketed under the trade name EMPILAN® by the company HUNTSMAN
- the monoethanolamide of copra acids, such as the amide marketed under the trade name MONAMID C M A® by the company CRODA.

In some embodiments, the fatty amide is chosen from monoethanolamide of stearic acid, monoisopropanolamide of copra acids, monoethanolamide of copra acids and N-oleoyldihydrosphingosine.

According to at least one embodiment, the fatty amide is a fatty amide that is solid at room temperature (25° C.).

According to at least one embodiment, the ready-to-use composition of the disclosure comprises at least one amide of alkanolamine and $C_{14}$-$C_{30}$ fatty acid and at least one ceramide.

Among the fatty substance, the ready-to-use composition can comprise an ester of $C_8$-$C_{30}$ fatty acids.

The at least one fatty acid ester is for example mono- or polyesters, such as chosen from the monoesters, diesters and triesters resulting from the reaction of linear or branched, saturated or unsaturated monoacids or diacids, having from 8 to 30 carbon atoms, optionally hydroxylated, with monohydric alcohols or polyols, saturated or unsaturated, linear, branched or cyclic, having from 2 to 1,000 carbon atoms and from 1 to 30 hydroxyl groups.

The fatty acids are for example chosen from stearic acid, palmitic acid, lauric acid, oleic acid, myristic acid.

The monohydric alcohols or polyols are for example chosen from ethanol, isopropanol, isooctanol, dodecanol, stearyl alcohol, ethylene glycol, propylene glycol, glycerol, polyethylene glycols, polypropylene glycols, glucose, methyl glucose, sorbitol, sorbitol anhydride, and pentaerythritol.

The monohydric alcohols and polyols, which are not polyethylene glycols and/or polypropylene glycols, can optionally be polyalkoxylated, and such as be polyethoxylated and/or polypropoxylated, the number of moles of ethylene oxide and/or of propylene oxide per mole of ester then for example ranging from 2 to 400, and further such as from 2 to 200.

For example, the monohydric alcohols or polyols, if they are different from polyethylene glycols and/or polypropylene glycols, are not polyalkoxylated.

The at least one fatty acid ester according to the disclosure can be non-ionic, i.e. they may not have ionic charges.

As examples of fatty acid esters according to the disclosure, mentions can be made of isopropyl myristate, stearyl stearate, myristate or palmitate, mono- or distearate of ethylene glycol, mono- or distearate of polyethylene glycols such as PEG-40 stearate, sorbitan monopalmitate, glyceryl isostearate, propylene glycol dipelargonate, 2-ethylhexyl palmitate, sorbitan tristearate, di(2-ethylhexyl) sebacate, glyceryl trihydroxystearate, cetyl stearate, palmitate or myristate, myristyl stearate, palmitate or myristate, or isononyl isononanoate.

According to at least one embodiment, the fatty acid ester is an ester of fatty acid and of fatty alcohol, the acid and the alcohol comprising from 6 to 30 carbon atoms.

As examples of fatty acid esters, mentions can be made of the esters and di-esters of sugars and of fatty acids. As used herein, "sugar" means oxidized hydrocarbon compounds that have several alcohol functions, with or without an aldehyde or ketone function, and have at least 4 carbon atoms. These sugars can be monosaccharides, oligosaccharides or polysaccharides.

As examples of sugars mentions can be made of sucrose, glucose, galactose, ribose, fucose, maltose, fructose, mannose, arabinose, xylose, lactose, and their derivatives for example alkylated, such as the methylated derivatives such as methylglucose.

The esters of sugars and of fatty acids can for example be chosen from the esters or mixtures of esters of sugars described previously and of fatty acids, for example $C_{12}$-$C_{22}$, linear or branched, saturated or unsaturated. If they are unsaturated, these compounds can comprise one to three conjugated or unconjugated carbon-carbon double bonds.

The esters according to at least one embodiment can also be chosen from the mono-, di-, tri- and tetra-esters, the polyesters and mixtures thereof.

These esters can be for example oleate, laurate, palmitate, myristate, behenate, cocoate, stearate, linoleate, linolenate, caprate, arachidonate esters, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

As an example, mention can be made of the product sold under the name GLUCATE® DO by the company Amerchol, which is a dioleate of methylglucose.

Non-limiting mentions can also be made of esters or of mixtures of esters of sugar of fatty acid:

the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the monolaurate of sucrose;

the products sold under the name Ryoto Sugar Esters for example with the reference 8370 and corresponding to the behenate of sucrose formed from 20% of monoester and 80% of di-triester-polyester;

the sucrose mono-di-palmito-stearate marketed by the company Goldschmidt under the name TEGOSOFT® PSE.

For example, the at least one fatty acid ester is chosen from ethylene glycol distearate, stearyl stearate, palmitate and myristate, cetyl stearate, palmitate and myristate, myristyl stearate, palmitate and myristate.

According to at least one embodiment, the at least one fatty acid ester is a fatty ester that is solid at room temperature.

The at least one fatty substance chosen from fatty amides and f fatty acid esters is present in an amount ranging from 0.01 to 50 wt. %, such as from 0.1 to 30 wt. %, and further such as from 0.2 to 10 wt. %, relative to the total weight of the composition.

The ready-to-use composition of the disclosure can comprise other fatty substances so as to reach the amount of at least 25%. The ready-to-use composition according to the disclosure for example has a total amount of fatty substance ranging from 25 to 85 wt. %, such as from 25 to 65%, and further such as from 30 to 55 wt. % relative to the total weight of the ready-to-use composition.

The fatty substance other than the fatty amides and the fatty acid esters previously defined are for example chosen from the lower alkanes, fatty alcohols, esters of fatty alcohol, non-silicone oils such as mineral, vegetable, animal and synthetic oils, the non-silicone and silicone waxes.

According to at least one embodiment, the fatty substance comprise at least one linear or branched, saturated or unsaturated hydrocarbon group, with 6 to 30 carbon atoms, optionally substituted, such as with at least one hydroxyl groups (for example 1 to 4). If they are unsaturated, these compounds can comprise one to three conjugated or unconjugated carbon-carbon double bonds.

Regarding the lower alkanes, they may have from 6 to 30 carbon atoms and are linear or branched, optionally cyclic. For example, the alkanes can be chosen from hexane and dodecane, and isoparaffins such as isohexadecane and isodecane.

As non-silicone oils usable for the disclosure, non-limiting mentions can be made of:

hydrocarbon oils of animal origin, such as perhydrosqualene;

hydrocarbon oils of vegetable origin, such as the liquid triglycerides of fatty acids having from 6 to 30 carbon atoms such as the triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, the triglycerides of caprylic/capric acids such as those sold by the company Stearineries Dubois or those sold under the names MIGLYOL® 810, 812 and 818 by the company Dynamit Nobel, jojoba oil, shea butter oil;

linear or branched hydrocarbons, of mineral or synthetic origin, paraffin oils, petroleum jelly, liquid paraffin, polydecenes, hydrogenated polyisobutene such as PARLEAM®;

fluorinated oils; non-limiting mentions can be made of perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoromethoxybutane and nonafluoroethoxyisobutane; the derivatives of perfluoromorpholine, such as 4-trifluoromethyl perfluoromorpholine sold under the name "PF 5052®" by the 3M Company.

The fatty alcohols according to at least one embodiment are non-alkoxylated. They are saturated or unsaturated, linear or branched, and have from 6 to 30 carbon atoms and such as from 8 to 30 carbon atoms; non-limiting mentions can be made of cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The non-silicone wax or waxes according to at least one embodiment are for example chosen from carnauba wax, candelilla wax, and Alfa wax, paraffin wax, ozokerite, vegetable waxes such as olive wax, rice wax, hydrogenated jojoba wax and absolute waxes of flowers such as essential wax of blackcurrant flower sold by the company BERTIN (France), animal waxes such as beeswaxes, and modified beeswaxes (cerabellina); other waxes or waxy raw materials for example can be chosen marine waxes such as that sold by the company SOPHIM under reference M82, and waxes of polyethylene or of polyolefins in general.

The esters other than those defined previously can be the esters of aliphatic saturated or unsaturated, linear or branched $C_1$-$C_7$ mono- or polyacids and of aliphatic saturated or unsaturated, linear or branched $C_1$-$C_{26}$ mono- or polyalcohols, the total number of carbons of the esters being for example greater than or equal to 10.

Among the monoesters, mentions can be made of cetyl lactate; $C_{12}$-$C_{15}$ alkyl lactate; isostearyl lactate; lauryl lactate; linoleyl lactate; and oleyl lactate.

According to at least one embodiment, it is also possible to use the esters of $C_4$-$C_7$ di- or tricarboxylic acids and of $C_1$-$C_{22}$ alcohols and the esters of $C_4$-$C_7$ mono-, di- or tricarboxylic acids and of $C_2$-$C_{26}$ di-, tri-, tetra- or pentahydroxy alcohols.

Non-limiting mentions can be made of: diisopropyl adipate; di-n-propyl adipate; dioctyl adipate; diisostearyl adipate; dioctyl maleate; triisopropyl citrate; triisotearyl citrate; glyceryl trilactate; trioctyldodecyl citrate; and trioleyl citrate.

Further non-limiting mention can be made of dioctyl malate.

The fatty substance can comprise silicones. The silicones can be volatile or non-volatile silicones, cyclic, linear or branched, unmodified or modified with organic groups, having a viscosity ranging from 5.10-6 to 2.5 m2/s at 25° C. and such as from 1.10-5 to 1 m2/s.

The silicones can be in the form of oils, waxes, resins or gums.

For example, the silicone can be chosen from the polydialkylsiloxanes, such as the polydimethylsiloxanes (PDMS), and the organo-modified polysiloxanes having at least one functional group chosen from poly(alkoxylated) groups, amine groups and alkoxy groups.

The organopolysiloxanes are defined in more detail in the work by Walter NOLL "Chemistry and Technology of Silicones" (1968), Academic Press. They can be volatile or non-volatile.

When they are volatile, the silicones are for example chosen from those having a boiling point ranging from 60° C. to 260° C., and for further example chosen from:

(i) the cyclic polydialkylsiloxanes having from 3 to 7, such as from 4 to 5 silicon atoms. These are, for example, octamethylcyclotetrasiloxane such as the one marketed under the name VOLATILE SILICONE® 7207 by UNION CARBIDE or SILBIONE® 70045 V2 by RHODIA, decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of formula:

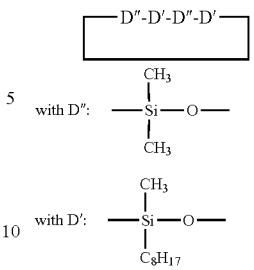

Non-limiting mentions can also be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bis-neopentane.

Other non-limiting examples of volatile silicones include the volatile linear polydialkylsiloxanes with 2 to 9 silicon atoms and having a viscosity less than or equal to $5.10^{-6}$ m$^2$/s at 25° C. These include, for example, decamethyltetrasiloxane such as the one marketed under the name "SH 200" by the company TORAY SILICONE. Other silicones in this class are described in the article published in Cosmetics and Toiletries, Vol. 91, Jan. 76, p. 27-32—TODD & BYERS "Volatile Silicone fluids for cosmetics".

According to at least one embodiment, non-volatile polydialkylsiloxanes, gums and resins of polydialkylsiloxanes, polyorganosiloxanes modified by the aforementioned organofunctional groups, and mixtures thereof, are used.

These silicones are for example chosen from the polydialkylsiloxanes, among which non-limiting mention can be made of the polydimethylsiloxanes with trimethylsilyl end groups. The viscosity of the silicones is measured at 25° C. according to standard ASTM 445 Appendix C.

Among these polydialkylsiloxanes, non-limiting mention can be made of the following commercial products:

the SILBIONE® oils of series 47 and 70 047 or the MIRASIL® oils marketed by RHODIA such as, for example, the oil 70 047 V 500 000;

the oils of the MIRASIL® series marketed by the company RHODIA;

the oils of the 200 series from the company DOW CORNING such as DC200, with a viscosity of 60 000 mm$^2$/s;

the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name dimethiconol (CTFA), such as the oils of the 48 series from the company RHODIA.

In this class of polydialkylsiloxanes, non-limiting mention can be made of the products marketed under the names "ABIL WAX® 9800 and 9801" by the company GOLDSCHMIDT, which are polydialkyl($C_1$-$C_{20}$) siloxanes.

The silicone gums can be polydialkylsiloxanes, such as polydimethylsiloxanes having high number-average molecular weights ranging from 200,000 to 1,000,000 used alone or mixed in a solvent. The solvent can be chosen from the volatile silicones, polydimethylsiloxane (PDMS) oils, polyphenylmethylsiloxane (PPMS) oils, isoparaffins, polyisobutylenes, methylene chloride, pentane, dodecane, tridecane and mixtures thereof.

Non-limiting mention can be made of:
mixtures formed from a chain end hydroxylated polydimethylsiloxane, or dimethiconol (CTFA) and from a cyclic polydimethylsiloxane also called cyclomethicone (CTFA), such as the product Q2 1401 marketed by the company DOW CORNING;
mixtures of a polydimethylsiloxane gum and a cyclic silicone such as the product SF 1214 Silicone Fluid from the company GENERAL ELECTRIC; this product is a gum SF 30 corresponding to a dimethicone, having a number-average molecular weight of 500,000 dissolved in the oil SF 1202 Silicone Fluid corresponding to decamethylcyclopentasiloxane; and
mixtures of two PDMS of different viscosities, and for example of a PDMS gum and a PDMS oil, such as the product SF 1236 from the company GENERAL ELECTRIC. The product SF 1236 is a mixture of a gum SE 30 defined above having a viscosity of 20 m²/s and an oil SF 96 with a viscosity of $5.10^{-6}$ m²/s. This product for example comprises 15% of gum SE 30 and 85% of oil SF 96.

The resins of organopolysiloxanes can be crosslinked siloxane systems comprising the units:
$R_2SiO_{2/2}$, $R_3SiO_{1/2}$, $RSiO_{3/2}$ and $SiO_{4/2}$
wherein R represents an alkyl having 1 to 16 carbon atoms. Among these products, non-limiting mention can be made of those wherein R denotes a $C_1$-$C_4$ lower alkyl group, more particularly methyl.

Among these resins, further non-limiting mention can be made of the product marketed under the name "DOW CORNING 593" or those marketed under the names "SILICONE FLUID SS 4230 and SS 4267" by the company GENERAL ELECTRIC, which are silicones with a dimethyl/trimethyl siloxane structure.

As further examples of the resins, mention can be made of the trimethylsiloxysilicate type such as the one marketed under the names X22-4914, X21-5034 and X21-5037 by the company SHIN-ETSU.

The organomodified silicones can be silicones as defined previously and have in their structure at least one organofunctional group fixed via a hydrocarbon group.

In addition to the silicones described above, the organomodified silicones can be polydiaryl siloxanes, such as polydiphenylsiloxanes, and polyalkyl-arylsiloxanes functionalized by the organofunctional groups mentioned previously.

The polyalkylarylsiloxanes are chosen for example from the linear and branched polydimethyl/methylphenylsiloxanes and polydimethyl/diphenylsiloxanes with viscosity ranging from 1.10-5 to 5.10-2 m²/s at 25° C.

Among these polyalkylarylsiloxanes, non-limiting mention can be made of the products marketed under the following names:
the SILBIONE® oils of the 70 641 series from RHODIA;
the oils of the RHODORSIL® 70 633 and 763 series from RHODIA;
the oil DOW CORNING 556 COSMETIC GRADE FLUID from DOW CORNING;
the silicones of the PK series from BAYER such as the product PK20;
the silicones of the PN, PH series from BAYER such as the products PN1000 and PH1000;
certain oils of the SF series from GENERAL ELECTRIC such as SF 1023, SF 1154, SF 1250, SF 1265.

Among the organomodified silicones, non-limiting mentions can be made of the polyorganosiloxanes having:
polyethyleneoxy and/or polypropyleneoxy groups optionally comprising $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl($C_{12}$)-methicone copolyol marketed by the company DOW CORNING under the name Q2 5200;

substituted or unsubstituted amine groups such as the products marketed under the name GP 4 Silicone Fluid and GP 7100 by the company GENESEE or the products marketed under the names Q2 8220 and DOW CORNING 929 or 939 by the company DOW CORNING. The substituted amine groups can be, for example, $C_1$-$C_4$ aminoalkyl groups; and alkoxylated groups, such as the product marketed under the name "SILICONE COPOLYMER F-755" by SWS SILICONES and ABIL WAX® 2428, 2434 and 2440 by the company GOLDSCHMIDT.

For example, the fatty substances other than the fatty amides and the fatty acid esters previously defined are chosen from the compounds that are liquid or pasty at room temperature and atmospheric pressure.

According to at least one embodiment, they are liquid at a temperature of 25° C. and at atmospheric pressure.

For example, the additional liquid fatty substance(s) are chosen from liquid paraffin, polydecenes, liquid esters of fatty acids or of fatty alcohols, and mixtures thereof, for example, the fatty substance(s) of the ready-to-use composition according to the disclosure are non-silicone.

The ready-to-use composition according to the disclosure comprises at least one dye precursor.

The at least one dye precursor is chosen from oxidation bases and couplers.

The oxidation base or bases can be chosen from those known conventionally in oxidation dyeing, and among which non-limiting mention can be made of the ortho- and para-phenylenediamines, double bases, ortho- and para-aminophenols, heterocyclic bases and the acid addition salts thereof.

These oxidation bases can for example be cationic.

The para-phenylenediamines can for example be chosen from the compounds of formula (II) and acid addition salts thereof:

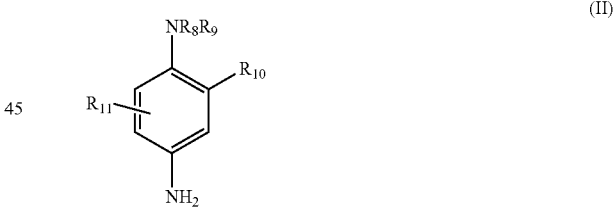

(II)

wherein:
$R_8$ represents a hydrogen atom, a $C_1$-$C_4$ alkyl, $C_1$-$C_4$ monohydroxyalkyl, $C_2$-$C_4$ polyhydroxyalkyl, alkoxy($C_1$-$C_4$)alkyl ($C_1$-$C_4$), $C_1$-$C_4$ alkyl radical substituted with a nitrogen-containing, phenyl or 4'-aminophenyl group;
$R_9$ represents a hydrogen atom, a $C_1$-$C_4$ alkyl, $C_1$-$C_4$ monohydroxyalkyl, $C_2$-$C_4$ polyhydroxyalkyl, alkoxy($C_1$-$C_4$)alkyl ($C_1$-$C_4$) or $C_1$-$C_4$ alkyl radical substituted with a nitrogen-containing group;
$R_8$ and $R_9$ can also form, with the nitrogen atom carrying them, a nitrogen-containing 5 or 6 membered heterocycle optionally substituted with at least one group chosen from alkyl, hydroxy and ureido;
$R_{10}$ represents a hydrogen atom, a halogen atom such as a chlorine atom, a $C_1$-$C_4$ alkyl, sulpho, carboxy, $C_1$-$C_4$ monohydroxyalkyl or $C_1$-$C_4$ hydroxyalkoxy, $C_1$-$C_4$ acetylaminoalkoxy, $C_1$-$C_4$ mesylaminoalkoxy or $C_1$-$C_4$ carbamoylaminoalkoxy radical;

$R_{11}$ represents a hydrogen atom, a halogen atom or a $C_1$-$C_4$ alkyl radical.

Among the nitrogen-containing groups of the above formula (II), non-limiting mention can be made of the amino, monoalkyl($C_1$-$C_4$)amino, dialkyl($C_1$-$C_4$)amino, trialkyl($C_1$-$C_4$)amino, monohydroxyalkyl($C_1$-$C_4$)amino, imidazolinium and ammonium radicals.

Among the para-phenylenediamines of the above formula (II), non-limiting mention can be made of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, 4-N,N-bis-(β-hydroxyethyl)amino-2-methyl-aniline, N,N-bis-β-hydroxyethyl paraphenylenediamine, 4-N,N-bis-(β-hydroxyethyl)-amino-2-chloro-aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and acid addition salts thereof.

Among the para-phenylenediamines of the above formula (II), further non-limiting mention can be made of para-phenylenediamine, para-toluoylenediamine, 2-isopropyl-para-phenylenediamine, 2-β-hydroxyethyl-para-phenylenediamine, 2,6-dimethyl-para-phenylene-diamine, 2,6-diethyl-para-phenylenediamine, 2,3-dimethyl-para-phenylenediamine, 2-chloro-para-phenylenediamine, N,N-bis-β-hydroxyethyl paraphenylenediamine and acid addition salts thereof.

Even further non-limiting mention can be made of para-phenylenediamine, para-toluoylenediamine, N,N-bis-β-hydroxyethyl paraphenylenediamine, and acid addition salts thereof.

According to the disclosure, double bases, for example, are compounds having at least two aromatic nuclei, bearing amino and/or hydroxyl groups.

Among the double bases usable as oxidation bases in the ready-to-use composition according to the disclosure, non-limiting mention can be made of the compounds of formula (III) and acid addition salts thereof:

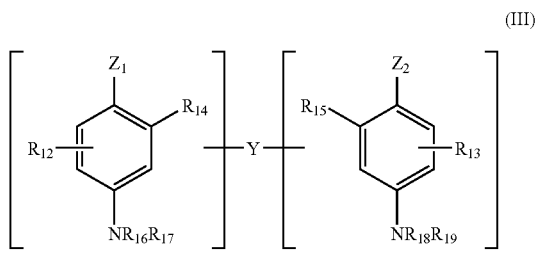

(III)

wherein:

$Z_1$ and $Z_2$, which may be identical or different, represent a hydroxyl or —$NH_2$ radical, which can be substituted with a $C_1$-$C_4$ alkyl radical or with a linkage Y;

the linkage Y represents a linear or branched alkylene chain having from 1 to 14 carbon atoms, which can be interrupted or terminated by at least one nitrogen-containing group and/or by at least one heteroatom such as oxygen, sulphur or nitrogen atoms, and optionally substituted with at least one hydroxyl or $C_1$-$C_6$ alkoxy radical;

$R_{12}$ and $R_{13}$ represent a hydrogen atom or a halogen atom, a $C_1$-$C_4$ alkyl, $C_1$-$C_4$ monohydroxyalkyl, $C_2$-$C_4$ polyhydroxyalkyl, $C_1$-$C_4$ aminoalkyl radical or a linkage Y;

$R_{14}$, $R_{15}$, $R_{16}$, $R_{17}$, $R_{18}$ and $R_{19}$, which may be identical or different, represent a hydrogen atom, a linkage Y or a $C_1$-$C_4$ alkyl radical;

it being understood that the compounds of formula (III) only have a single linkage Y per molecule.

Among the nitrogen-containing groups of the above formula (III), non-limiting mention can be made of the amino, monoalkyl(C1-C4)amino, dialkyl(C1-C4)amino, trialkyl(C1-C4)amino, monohydroxyalkyl(C1-C4)amino, imidazolinium and ammonium radicals.

Among the double bases of the above formula (III), non-limiting mention can be made of N,N'-bis-(β-hydroxyethyl)-N,N'-bis-(4'-aminophenyl)-1,3-diaminopropanol, N,N'-bis-(β-hydroxyethyl)-N,N'-bis-(4'-aminophenyl)-ethylenediamine, N,N'-bis-(4-aminophenyl)-tetramethylenediamine, N,N'-bis-(β-hydroxyethyl)-N,N'-bis-(4-aminophenyl)-tetramethylenediamine, N,N'-bis-(4-methyl-aminophenyl)-tetramethylenediamine, N,N'-bis-(ethyl)-N,N'-bis-(4'-amino-3'-methylphenyl)-ethylenediamine, 1,8-bis-(2,5-diaminophenoxy)-3,5-dioxaoctane, and acid addition salts thereof.

Among these double bases of formula (III), further non-limiting mention can be made of N,N'-bis-(β-hydroxyethyl)-N,N'-bis-(4'-aminophenyl)-1,3-diaminopropanol, 1,8-bis-(2,5-diaminophenoxy)-3,5-dioxaoctane or acid addition salts thereof.

The para-aminophenols can for example be chosen from the compounds of formula (IV) and acid addition salts thereof:

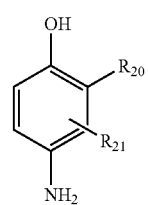

(IV)

wherein:

$R_{20}$ represents a hydrogen atom, a halogen atom such as fluorine, a $C_1$-$C_4$ alkyl, $C_1$-$C_4$ monohydroxyalkyl, alkoxy($C_1$-$C_4$)alkyl($C_1$-$C_4$) or $C_1$-$C_4$ aminoalkyl, or hydroxyalkyl($C_1$-$C_4$)$C_1$-$C_4$ aminoalkyl radical;

$R_{21}$ represents a hydrogen atom or a halogen atom such as fluorine, a $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl or alkoxy($C_1$-$C_4$)alkyl($C_1$-$C_4$) radical.

Among the para-aminophenols of the above formula (IV), non-limiting mention can be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)-phenol, and their salts of addition with an acid.

Further exemplary mention can be made of para-aminophenol and 4-amino-3-methylphenol.

The ortho-aminophenols usable as oxidation bases are for example chosen from 2-aminophenol, 2-amino-1-hydroxy-5-methylbenzene, 2-amino-1-hydroxy-6-methylbenzene, 5-acetamido-2-aminophenol, and acid addition salts thereof.

Among the heterocyclic bases usable as oxidation bases in the ready-to-use composition according to the disclosure, non-limiting mention can be made of pyridine derivatives, pyrimidine derivatives, pyrazole derivatives, and acid addition salts thererof.

Among the pyridine derivatives, non-limiting mention can be made of the compounds described for example in Great Britain Patent Nos. 1 026 978 and 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and acid addition salts thereof.

Among the pyrimidine derivatives, non-limiting mentions can be made of the compounds described for example in German Patent Nos. 2 359 399 or Japanese Patent Nos. 88-169 571 and 91-10659 or PCT Patent Application Publication No. WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolo-pyrimidine derivatives such as those mentioned in French Patent Application Publication No. 2 750 048 and among which mention can be made of pyrazolo-[1,5-a]-pyrimidine-3,7-diamine; 2,5-dimethylpyrazolo-[1,5-a]-pyrimidine-3,7-diamine; pyrazolo-[1,5-a]-pyrimidine-3,5-diamine; 2,7-dimethylpyrazolo-[1,5-a]-pyrimidine-3,5-diamine; 3-aminopyrazolo-[1,5-a]-pyrimidin-7-ol; 3-aminopyrazolo-[1,5-a]-pyrimidin-5-ol; 2-(3-amino pyrazolo-[1,5-a]-pyrimidin-7-ylamino)-ethanol; 2-(7-aminopyrazolo-[1,5-a]-pyrimidin-3-ylamino)-ethanol; 2-[(3-aminopyrazolo[1,5-a]pyrimidin-7-yl)-(2-hydroxy-ethyl)-amino]-ethanol; 2-[(7-aminopyrazolo[1,5-a]pyrimidin-3-yl)-(2-hydroxy-ethyl)-amino]-ethanol; 5,6-dimethylpyrazolo-[1,5-a]-pyrimidine-3,7-diamine; 2,6-dimethylpyrazolo-[1,5-a]-pyrimidine-3,7-diamine; 2,5,N7,N7-tetramethylpyrazolo-[1,5-a]-pyrimidine-3,7-diamine; 3-amino-5-methyl-7-imidazolylpropylaminopyrazolo-[1,5-a]-pyrimidine; addition salts thereof and tautomeric forms thereof, when there is tautomeric equilibrium.

Among the pyrazole derivatives, non-limiting mention can be made of the compounds described in German Patent Nos. 3 843 892, 4 133 957 and 195 43 988, PCT Patent Application Publication No. WO 94/08969 and WO 94/08970, and French Application Publication No. 2 733 749, such as the 4,5-diaminopyrazoles, for example 4,5-diamino-1-methylpyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)-pyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole; 3,4-diaminopyrazole; 4-amino-1,3-dimethyl-5-hydrazino-pyrazole; 3,4,5-triaminopyrazoles such as for example 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole; and acid addition salts thereof.

Exemplary mention can be made of 4,5-diaminopyrazole, and further exemplary mention can be made of 4,5-diamino-1-(β-hydroxyethyl)-pyrazole and/or a salt thereof.

As pyrazole derivatives, non-limiting mention can be made of diamino-N,N-dihydropyrazolopyrazolones and such as those described in French Application Publication No. 2 886 136 such as the following compounds and addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydro-pyrazol-3-one, 4,5-diamino-1,2-diethyl-1,2-dihydro-pyrazol-3-one, 4,5-diamino-1,2-di-(2-hydroxyethyl)-1,2-dihydro-pyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydro-pyrazol-3-one, 4-amino-5-(3-dimethylamino-pyrrolidin-1-yl)-1,2-diethyl-1,2-dihydro-pyrazol-3-one, and 2,3-diamino-6-hydroxy-6,7-dihydro-1H,5H-pyrazolo[1,2-a]pyrazol-1-one.

Exemplary mention can be made of 2,3-diamino-6,7-dihydro-1H,5H-pyrazolo[1,2-a]pyrazol-1-one and/or addition salts thereof.

As heterocyclic bases, exemplary mention can be made of 4,5-diamino-1-(β-hydroxyethyl)pyrazole and/or 2,3-diamino-6,7-dihydro-1H,5H-pyrazolo[1,2-a]pyrazol-1-one and/or addition salts thereof.

As cationic oxidation bases usable in the ready-to-use compositions according to the disclosure, mention can be made, for example, the following compounds: the para-phenylenediamines such as those described in French Patent Application Publication Nos. 2 766 177 and 2 766 178, the para-aminophenols as described for example in French Patent Application Publication Nos. 2 766 177 and 2 766 178, the ortho-phenylenediamines as described for example in French Patent Application Publication Nos. 2 782 718, 2 782 716 and 2 782 719, ortho-aminophenols or cationic double bases such as derivatives of the bis(aminophenyl)alkylenediamine type described in French Patent Application Publication No. 2 766 179, as well as the cationic heterocyclic bases, the compounds having at least one quaternary nitrogen atom.

For example, the cationic oxidation bases usable in the ready-to-use compositions according to the disclosure are cationic para-phenylenediamines.

According to at least one embodiment, the ready-to-use composition comprises cationic oxidation bases of para-phenylenediamine structure, wherein at least one of the amine functions is a tertiary amine bearing a pyrrolidine nucleus, the molecule possessing at least one quaternized nitrogen atom. Such bases are described, for example, in European Patent Application Publication No. 1 348 695.

The ready-to-use composition according to the disclosure, for example, comprises a total amount of oxidation bases ranging from 0.0005 to 12 wt. % relative to the total weight of the ready-to-use composition. For further example, it comprises a total amount of oxidation bases ranging from 0.005 to 8 wt. %, and such as from 0.05 to 5 wt. %, relative to the total weight of said composition.

The coupler or couplers usable in the ready-to-use composition according to the disclosure can be those used conventionally in compositions for oxidation dyeing, i.e. meta-aminophenols, meta-phenylenediamines, metadiphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and acid addition salts thereof.

These couplers are for example chosen from 2,4-diamino-1-β-hydroxyethyloxy)-benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis-(2,4-diaminophenoxy)-propane, sesamol, 1-amino-2-methoxy-4,5-methylenedioxybenzene, α-naphthol, 6-hydroxy-indole, 4-hydroxy-indole, 4-hydroxy-N-methyl indole, 6-hydroxy-indoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo-[3,2-c]-1,2,4-triazole, 2,6-dimethylpyrazolo-[1,5-b]-1,2,4-triazole and acid addition salts thereof.

The ready-to-use composition according to the disclosure may comprise a total amount of couplers ranging from 0.0001 to 15 wt. % relative to the total weight of the composition. For example, it comprises a total amount of couplers ranging from 0.001 to 10 wt. %, and such as from 0.01 to 8 wt. %, relative to the total weight of the composition.

The oxidation bases and couplers can be present in the ready-to-use compositions of the disclosure in the form of addition salts thereof, and such as in the form of acid addition salts thereof.

The acid addition salts that can be used for the application of the disclosure are, for example, chosen from hydrochlorides, hydrobromides, sulphates, citrates, succinates, tartrates, lactates, acetates, alkylsulphates and alkylsulphonates.

When the oxidation bases or the couplers comprise at least one carboxylic or sulphonic acid function, base addition salts thereof may be used. The base addition salts usable in the dyeing compositions of the disclosure can then, for example, be chosen from those obtained with sodium hydroxide, potassium hydroxide, ammonia and amines.

According to at least one embodiment of the disclosure, the ready-to-use composition comprises at least one oxidation base and at least one coupler.

According to at least one embodiment, the additional oxidation base is chosen from para-aminophenols, heterocyclic bases and acid addition salts thereof.

The ready-to-use composition according to the present disclosure comprises at least one oxidizing agent.

The at least one oxidizing agent is chosen for example from the peroxides such as hydrogen peroxide, urea peroxide, the bromates or ferricyanides of alkali metals, the persalts such as perborates, percarbonates and persulphates. It is also possible to use, as oxidizing agent, at least one oxidation-reduction enzyme such as laccases, peroxidases and oxidoreductases with 2 electrons (such as uricase), optionally in the presence of their respective donor or cofactor.

Exemplary mention can be made of peroxide. This oxidizing agent is for example constituted of a solution of hydrogen peroxide, the strength of which can vary, such as, from about 1 to 40 volumes, and further such as from about 5 to 40 volumes.

The concentration of the at least one oxidizing agent of the ready-to-use composition of the disclosure, for example, ranges from 0.1 to 20% and such as ranges from 0.5 to 10% by weight relative to the total weight of the ready-to-use composition.

The ready-to-use composition of the disclosure, for example, comprises at least one alkaline agent. The at least one alkaline agent is for example chosen from ammonia, carbonates and bicarbonates of alkali metals and such as sodium or potassium, alkanolamines such as mono-, di- and triethanolamines and their derivatives, hydroxyalkylamines and ethoxylated and propoxylated ethylenediamines, hydroxides of sodium and of potassium, amino acids and for example basic amino acids such as arginine and lysine and compounds of formula (V):

wherein:

R is a propylene residue optionally substituted with a hydroxyl group or a $C_1$-$C_4$ alkyl radical;

$R_{22}$, $R_{23}$, $R_{24}$ and $R_{25}$, which may be identical or different, represent a hydrogen atom, a $C_1$-$C_4$ alkyl or $C_1$-$C_4$ hydroxyalkyl radical.

According to at least one embodiment, the ready-to-use composition comprises as alkaline agent at least one organic amine, such as at least one alkanolamine. When the ready-to-use composition comprises more than one alkaline agents including an alkanolamine and ammonium hydroxide or salts thereof, the amount of organic amine(s) are for example higher than the amount of ammonia.

According to at least one embodiment, the ready-to-use composition comprises a small amount of ammonia, or even no ammonia. According to this embodiment, the ready-to-use composition for example comprises at least one alkanolamines, such as monoethanolamine.

The amount of the at least one alkaline agent of the ready-to-use composition of the disclosure, for example, ranges from 0.01 to 30%, and such as from 0.1 to 20% by weight relative to the total weight of the ready to use composition.

The ready-to-use composition according to the disclosure can moreover comprise direct dyes which can for example be chosen from the nitro dyes of the benzene series, the azo direct dyes, the methine direct dyes, and addition salts thereof. These direct dyes can be of non-ionic, anionic or cationic character.

The ready-to-use composition can also comprise other compounds constituting the coloring medium. This coloring medium may comprise water or a mixture of water and at least one acceptable organic solvent, such as water-soluble in the cosmetics field.

As examples of organic solvents, mention can be made of the alcohols such as ethyl alcohol, isopropyl alcohol, benzyl alcohol, and phenylethyl alcohol, or glycols or glycol ethers such as, for example, monomethyl, monoethyl and monobutyl ethers of ethylene glycol; propylene glycol or its ethers such as, for example, monomethyl ether of propylene glycol; butylene glycol, hexylene glycol, dipropylene glycol as well as alkyl ethers of diethylene glycol, for example monoethyl ether or monobutyl ether of diethylene glycol. The solvents can then be present in an amount ranging from about 0.01 to 35 wt. % and, such as, from about 0.1 to 25 wt % relative to the total weight of the ready-to-use composition.

For example, the ready-to-use composition of the disclosure may comprise water. For further example, the amount of water can range from 10 to 70%, and such as from 20 to 55% by weight relative to the total weight of the composition.

The ready-to-use composition according to the disclosure can further comprise at least one additive used conventionally in compositions for dyeing the hair.

"Additive" means a substance that is added, that is different from the aforementioned compounds.

As examples of additives that can be used, mention can be made of anionic, cationic, non-ionic, amphoteric, zwitterionic surfactants or mixtures thereof; anionic, cationic, non-ionic, amphoteric, zwitterionic polymers; mineral or organic thickening agents, and for example the anionic, cationic, non-ionic and amphoteric associative polymeric thickeners, other than the associative celluloses according to the disclosure; antioxidants or reducing agents; penetrating agents; sequestering agents; perfumes; buffers; dispersants; conditioners such as for example volatile or non-volatile, modified or unmodified silicones; film-forming agents; ceramides; preservatives; opacifiers; and antistatic agents.

The above additives can be present in an amount for each of them ranging from 0.01 to 20 wt. % relative to the total weight of the ready-to-use composition.

For example, the ready-to-use composition of the disclosure may comprise at least one surfactant.

As a further example, the at least one surfactant can be chosen from non-ionic surfactants and anionic surfactants.

The anionic surfactants are for example chosen from salts (for example salts of alkali metals, such as salts of sodium, salts of ammonium, salts of amines such as salts of aminoalcohols and salts of alkaline-earth metals such as magnesium) of the following compounds:

alkylsulphates, alkylether sulphates, alkylamidoether sulphates, alkaryl-polyether sulphates, monoglyceride sulphates;

alkylsulphonates, alkylamidesulphonates, alkylarylsulphonates, α-olefin-sulphonates, paraffin-sulphonates;

alkylphosphates, alkyletherphosphates;

alkylsulphosuccinates, alkylether sulphosuccinates, alkylamide-sulphosuccinates;

alkylsulphosuccinamates;

alkylsulphoacetates;

acylsarcosinates; acylisethionates and N-acyltaurates;

salts of fatty acids such as oleic, ricinoleic, palmitic, stearic acids, acids of copra oil or of hydrogenated copra oil;

salts of alkyl-D-galactoside uronic acids;

acyl-lactylates;

salts of polyalkoxylated alkyl ether carboxylic acids, polyalkoxylated alkaryl ether carboxylic acids, polyalkoxylated alkylamidoether carboxylic acids, such as those having from 2 to 50 ethylene oxide groups;

and mixtures thereof.

According to at least one embodiment, the alkyl or aryl radical of these various compounds may have from 6 to 24 carbon atoms, and for example from 8 to 24 carbon atoms, and the aryl radical for example denotes a phenyl or benzyl group.

The non-ionic surfactants are for example chosen from the mono- and poly-alkoxylated, mono- and poly-glycerolated non-ionic surfactants. The alkoxylated units are for example ethoxylated, propoxylated units, or a combination thereof, for example ethoxylated.

As examples of alkoxylated non-ionic surfactants, mention can be made of:

alkoxylated alkyl($C_8$-$C_{24}$)phenols, alkoxylated, saturated or unsaturated, linear or branched $C_8$-$C_{30}$ alcohols, alkoxylated, saturated or unsaturated, linear or branched $C_8$-$C_{30}$ amides, esters of saturated or unsaturated, linear or branched $C_8$-$C_{30}$ acids, and of polyethylene glycols, esters of saturated or unsaturated, linear or branched $C_3$-$C_{30}$ acids, and of polyethoxylated sorbitol, ethoxylated, saturated or unsaturated vegetable oils, condensates of ethylene oxide and/or propylene oxide, among others, alone or mixed.

The surfactants may have a number of moles of ethylene oxide and/or propylene oxide ranging from 1 to 50, such as from 2 to 30. In some embodiments, the non-ionic surfactants do not comprise propoxylated units.

According to at least one embodiment of the disclosure, the alkoxylated non-ionic surfactants are chosen from ethoxylated $C_8$-$C_{30}$, for example, ethoxylated $C_{18}$-$C_{30}$ alcohols.

As examples of mono- or poly-glycerolated non-ionic surfactants, mention can be made of mono- or poly-glycerolated $C_8$-$C_{40}$ alcohols.

Further, the mono- or poly-glycerolated $C_8$-$C_{40}$ alcohols can be chosen from compounds of the following formula:

$$RO-[CH_2-CH(CH_2OH)-O]_m-H$$

wherein R represents a linear or branched, $C_8$-$C_{40}$, such as $C_8$-$C_{30}$, alkyl or alkenyl radical, and m represents a number ranging from 1 to 30 and such as from 1 to 10.

As examples of compounds that are suitable for the application of the disclosure, mention can be made of lauric alcohol with 4 moles of glycerol (INCI name: POLYGLYCERYL-4 LAURYL ETHER), lauric alcohol with 1.5 moles of glycerol, oleic alcohol with 4 moles of glycerol (INCI name: POLYGLYCERYL-4 OLEYL ETHER), oleic alcohol with 2 moles of glycerol (INCI name: POLYGLYCERYL-2 OLEYL ETHER), cetearyl alcohol with 2 moles of glycerol, cetearyl alcohol with 6 moles of glycerol, oleocetyl alcohol with 6 moles of glycerol, and octadecanol with 6 moles of glycerol.

The alcohol can represent a mixture of alcohols, as the value of m represents a statistical value, which signifies that a commercial product can contain several species of polyglycerolated fatty alcohols in the form of a mixture.

Among the mono- or poly-glycerolated alcohols, mention can be made of $C_8/C_{10}$ alcohol with one mole of glycerol, $C_{10}/C_{12}$ alcohol with 1 mole of glycerol and $C_{12}$ alcohol with 1.5 mole of glycerol.

For example, the surfactant(s) present in the ready-to-use composition of the disclosure is a non-ionic surfactant(s).

The surfactant(s) can be present in the ready-to-use composition of the disclosure in an amount, for example, ranging from 0.1 to 50 wt. %, such as from 0.5 to 30 wt. % relative to the total weight of the ready-to-use composition.

Of course, a person skilled in the art will take care to choose the aforementioned optional additive(s) in such a way that the expected properties attaching intrinsically to the ready-to-use compositions according to the disclosure are not, or substantially not, adversely affected by the additive(s).

The pH of the ready-to-use composition according to the disclosure can range from about 3 to 12, such as from about 5 to 11, and further such as from 7 to 11. It can be adjusted to the desired value by means of acidifying or alkalizing agents usually employed in the dyeing of keratin fibers or alternatively by means of conventional buffer systems.

The alkaline agents are for example those described previously.

Among the acidifying agents, mention can be made of, as examples, mineral or organic acids such as hydrochloric acid, orthophosphoric acid, carboxylic acids such as tartaric acid, citric acid, lactic acid, or sulphonic acids.

The ready-to-use composition according to the disclosure can be in various forms, such as in the form of liquids, creams, gels, or in any other suitable form for carrying out dyeing of keratin fibers, and for example of human hair.

Provided herein is a method of dyeing of keratin fibers, comprising applying the ready-to-use composition to the keratin fibers. The color can be revealed at acid, neutral or alkaline pH and the oxidizing agent can be added at the moment of use or it can be applied simultaneously or sequentially with the other compounds of the ready-to-use composition of the disclosure.

After a holding time, for example, ranging from about 1 to 60 minutes, such as from about 5 to 45 minutes, the keratin fibers are rinsed, optionally washed with shampoo and rinsed again, and then dried.

The ready-to-use composition according to the disclosure can result from the mixing of at least two compositions and for example of 2 or 3 compositions, including for example an oxidizing composition comprising at least one oxidizing agent as defined previously. One of the compositions can be anhydrous.

Provided is also a multi-compartment kit or a dyeing "kit", comprising a first compartment which contains a composition comprising at least one fatty substance wherein at least one of the at least one fatty substance being chosen from fatty amides and fatty acid esters, a second compartment comprising at least one dye precursor and optionally at least one alkaline agent, and a third compartment comprising at least one oxidizing agent, and optionally at least one fatty substance.

In this embodiment, the composition comprising the at least one fatty substance wherein at least one of the at least one fatty substance being chosen from fatty amides and fatty acid esters can be anhydrous. Anhydrous composition means, in the sense of the disclosure, a cosmetic composition having a water content less than or equal to 5 wt. %, such as less than or equal to 2 wt % and further such as less than or equal to 1 wt. % relative to the weight of the composition. It should be noted that this relates for example to bound water, such as the water of crystallization of salts or traces of water absorbed by the raw materials used in the production of the compositions according to the disclosure.

Also provided is a multi-compartment kit, comprising a first compartment comprising at least one fatty substance wherein at least one of the at least one fatty substance being chosen from fatty amides and fatty acid esters and at least one oxidizing agent, and a second compartment comprising at least one dye precursor and optionally at least one alkaline agent. The kit can be equipped with an applicator for delivery of the desired mixture onto the hair, such as the devices described in French Patent Application No. 2 586 913.

Further provided is a multi-compartment kit, comprising a first compartment comprising at least one fatty substance wherein at least one of the at least one fatty substance being chosen from fatty amides and fatty acid esters, at least one dye precursor, and optionally at least one alkaline agent, and a second compartment comprising at least one oxidizing agent.

The examples given below are intended to illustrate the disclosure but without limiting the scope thereof.

EXAMPLES

The following compositions were prepared:

Example 1

| Composition 1 | Concentration (g %) |
| --- | --- |
| DISTEARDIMONIUM HECTORITE | 3 |
| OCTYLDODECANOL | 11.5 |
| GLYCOL DISTEARATE | 8 |
| LIQUID PARAFFIN | 64.488 |
| PROPYLENE CARBONATE | 1 |
| LAURETH-2 | 1 |
| POLYSORBATE 21 | 11 |
| N-OLEYL DI-HYDROSPHINGOSINE | 0.012 |

| Composition 2 | concentration (g %) |
| --- | --- |
| DIETHYLENETRIAMINE PENTAACETIC ACID, PENTASODIUM SALT IN AQUEOUS SOLUTION AT 40% | 1 |
| SODIUM METABISULPHITE | 0.7 |
| MONOETHANOLAMINE | 14.5 |
| 1-METHYL-2,5-DIAMINOBENZENE | 2.25 |
| 2,4-DIAMINOPHENOXYETHANOL HCl | 0.05 |
| 1,3-DIHYDROXYBENZENE (RESORCINOL) | 2 |
| m-AMINOPHENOL | 0.36 |
| NATROSOL 250 HHR (hydroxyethylcellulose) | 1.5 |
| HEXYLENE GLYCOL | 3 |
| DIPROPYLENE GLYCOL | 3 |
| ETHYL ALCOHOL | 8.25 |
| PROPYLENE GLYCOL | 6.2 |
| ASCORBIC ACID | 0.25 |
| WATER | Qs 100 g |

| Composition 3 | Concentration (g %) |
| --- | --- |
| DIETHYLENETRIAMINE PENTAACETIC ACID, PENTASODIUM SALT IN AQUEOUS SOLUTION AT 40% | 0.15 |
| HYDROGEN PEROXIDE IN SOLUTION AT 50% (HYDROGEN PEROXIDE 200 VOL.) | 12 |
| SODIUM STANNATE | 0.04 |
| SODIUM PYROPHOSPHATE | 0.03 |
| LIQUID PARAFFIN | 20 |
| HEXADIMETHRINE CHLORIDE (AS at 60% in water) | 0.25 |
| POLYQUATERNIUM-6 (AS at 40% in water) | 0.5 |
| GLYCEROL | 0.5 |
| CETYLSTEARYL ALCOHOL ($C_{16}/C_{18}$ 30/70) | 8 |
| ETHOXYLATED CETYLSTEARYL ALCOHOL (33 EO) | 3 |
| AMIDE OF ETHOXYLATED COLZA ACIDS (4 EO) PROTECTED at 92.3% in water | 1.3 |
| VITAMIN E | 0.1 |
| PHOSPHORIC ACID | Qs    pH2.2 |
| WATER | Qs    100 g |

Example 2

| Composition 1' | Concentration (g %) |
| --- | --- |
| DISTEARDIMONIUM HECTORITE | 3 |
| OCTYLDODECANOL | 11.5 |

-continued

| | |
|---|---|
| GLYCOL DISTEARATE | 4 |
| LIQUID PARAFFIN | 64.488 |
| PROPYLENE CARBONATE | 1 |
| LAURETH-2 | 1 |
| POLYSORBATE 21 | 11 |
| STEARAMIDE MEA(AND) MONOETHANOLAMINE (AND) STEARIC ACID (96/2/2) | 4 |
| N-OLEYL DI-HYDROSPHINGOSINE | 0.012 |

| Composition 2' | concentration (g %) |
|---|---|
| DIETHYLENETRIAMINE PENTAACETIC ACID, PENTASODIUM SALT IN AQUEOUS SOLUTION AT 40% | 1 |
| SODIUM METABISULPHITE | 0.7 |
| MONOETHANOLAMINE | 14.5 |
| 1-METHYL-2,5-DIAMINOBENZENE | 1.69 |
| 2-METHYL-5-HYDROXYETHYLAMINOPHENOL | 4.176 |
| 1-METHYL-2-HYDROXY-4-AMINO-BENZENE | 1.392 |
| 1,3-DIHYDROXYBENZENE (RESORCINOL) | 0.884 |
| p-AMINOPHENOL | 2.436 |
| NATROSOL 250 HHR (hydroxyethylcellulose) | 1.5 |
| DIPROPYLENE GLYCOL | 10 |
| ETHYL ALCOHOL | 15 |
| PROPYLENE GLYCOL | 5 |
| ASCORBIC ACID | 0.25 |
| WATER | Qs 100 g |

Composition 3' employed in Example 2 was identical to the composition 3 described in Example 1.

Compositions 1, 2 and 3 (for Example 1), and 1', 2' and 3' (for Example 2) were mixed at the moment of use in the following proportions: 10 g of composition 1 (or 1') with 4 g of composition 2 (or 2') and 16 g of composition 3 (or 3'). The mixture was applied on locks of natural grey hair at 90% of white hair at a rate of 10 g of mixture to 1 g of hair. After waiting 30 min, the hair was rinsed, washed with a standard shampoo and dried.

The hair coloring was evaluated visually.

| | |
|---|---|
| Example 1 | Natural light chestnut |
| Example 2 | Dark chestnut with mahogany red sheen |

What is claimed is:

1. A ready-to-use composition for the oxidation dyeing of keratin fibers, comprising
   A) at least one fatty substance present in a total amount ranging from 30% to 85% by weight relative to the total weight of the ready-to-use composition, at least one of the at least one fatty substance being chosen from fatty amides and fatty acid esters,
   B) at least one dye precursor,
   C) at least one oxidizing agent, and optionally
   D) at least one alkaline agent.

2. The ready-to-use composition according to claim 1, wherein the at least one fatty amide and/or the at least one fatty acid ester are solid at room temperature.

3. The ready-to-use composition according to claim 1, wherein the at least one fatty amide is an amide of a $C_2$-$C_{10}$ mono- or dialkanolamine, optionally substituted, and of a $C_9$-$C_{30}$ fatty acid.

4. The ready-to-use composition according to claim 1, wherein the at least one fatty amide is chosen from compounds of formula (I):

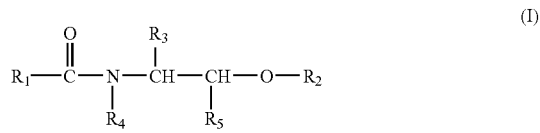

wherein:
$R_1$ denotes either
a linear or branched, saturated or unsaturated $C_9$-$C_{30}$ hydrocarbon radical, which is optionally substituted with at least one hydroxyl group, the at least one hydroxyl group being optionally esterified by a saturated or unsaturated $C_{16}$-$C_{30}$ fatty acid; or a radical R"—(NR—CO)—R', where R denotes a hydrogen atom; or a mono- or polyhydroxylated $C_1$-$C_{10}$ hydrocarbon radical, R' and R" are hydrocarbon radicals wherein the total number of carbon atoms ranges from 9 to 30, R' being a divalent radical;

$R_2$ denotes a hydrogen atom or a (glycosyl)$_n$, (galactosyl)$_m$ or sulphogalactosyl radical, wherein n is an integer ranging from 1 to 4 and m is an integer ranging from 1 to 8;

$R_3$ denotes a hydrogen atom or a saturated or unsaturated $C_{16}$-$C_{27}$ hydrocarbon radical, which is optionally substituted with at least one $C_1$-$C_{14}$ alkyl radical; or a $C_{15}$-$C_{26}$ α-hydroxyalkyl radical whose hydroxyl group is optionally esterified by a $C_{16}$-$C_{30}$ α-hydroxyacid;

$R_4$ denotes a hydrogen atom, a saturated or unsaturated $C_{16}$-$C_{27}$ hydrocarbon radical, a $C_2$-$C_6$ hydroxyalkyl radical or a radical —CH$_2$—CHOH—CH$_2$—O—R$_6$ wherein $R_6$ denotes a $C_{10}$-$C_{26}$ hydrocarbon radical; and $R_5$ denotes a hydrogen atom or a mono- or polyhydroxylated $C_1$-$C_4$ hydrocarbon radical.

5. The ready-to-use composition according to claim 4, wherein $R_1$ denotes a radical R"—(NR—CO)—R', where R denotes a monohydroxylated $C_1$-$C_{10}$ hydrocarbon radical, R' and R" are hydrocarbon radicals wherein the total number of carbon atoms ranges from 9 to 30, R' being a divalent radical.

6. The ready-to-use composition according to claim 4, wherein the at least one fatty amide is chosen from ceramides of formula (I), wherein $R_1$ denotes a saturated or unsaturated alkyl radical derived from $C_{16}$-$C_{22}$ fatty acids, optionally hydroxylated; $R_2$ denotes a hydrogen atom; and $R_3$ denotes a $C_{16}$ α-hydroxyalkyl radical.

7. The ready-to-use composition according to claim 1, wherein the at least one fatty amide is chosen from monoethanolamide of stearic acids, monoisopropanolamide of copra acids, monoethanolamide of copra acids and N-oleoyldihydrosphingosine.

8. The ready-to-use composition according to claim 1, wherein the at least one fatty acid ester is obtained from $C_8$-$C_{30}$ fatty acids.

9. The ready-to-use composition according to claim 8, wherein the at least one fatty acid ester is chosen from esters of stearic acid, palmitic acid, lauric acid, oleic acid, and myristic acid.

10. The ready-to-use composition according to claim 1, wherein the at least one fatty acid ester is chosen from ethylene glycol distearate, stearyl stearate, palmitate or myristate, cetyl stearate, palmitate or myristate, myristyl stearate, palmitate and myristate.

11. The ready-to-use composition according to claim 1, wherein at least one of the at least one fatty substance is chosen from fatty amides and fatty acid esters, and is present in an amount ranging from 0.01 to 50 wt. % relative to the total weight of the ready-to-use composition.

12. The ready-to-use composition according to claim 11, wherein at least one of the at least one fatty substance is chosen from fatty amides and fatty acid esters, and is present in an amount ranging from 0.1 to 30 wt. % relative to the total weight of the ready-to-use composition.

13. The ready-to-use composition according to claim 11, wherein at least one of the at least one fatty substance is chosen from fatty amides and fatty acid esters, and is present in an amount ranging from 0.2 to 10 wt. % relative to the total weight of the ready-to-use composition.

14. The ready-to-use composition according to claim 1, wherein the at least one dye precursor is chosen from oxidation bases and couplers.

15. The ready-to-use composition according to claim 1, wherein the at least one dye precursor is chosen from ortho- and para-phenylenediamine oxidation bases, double bases, ortho- and para-aminophenols, heterocyclic bases, meta-aminophenols, meta-phenylenediamines, meta-diphenols, naphthols, heterocyclic couplers, and acid addition salts thereof.

16. The ready-to-use composition according to claim 1, wherein the at least one oxidizing agent is a peroxide.

17. The ready-to-use composition according to claim 16, wherein the at least one oxidizing agent is hydrogen peroxide.

18. The ready-to-use composition according to claim 1, wherein the at least one alkaline agent is chosen from ammonia and alkanolamines.

19. The ready-to-use composition according to claim 18, wherein the at least one alkaline agent is chosen from alkanolamines.

20. The ready-to-use composition according to claim 1, wherein the at least one alkaline agent is monoethanolamine.

21. A method of dyeing of keratin fibers, comprising applying a ready-to-use composition to the keratin fibers for a sufficient time to develop the desired coloration,
wherein the ready-to-use composition comprises
A) at least one fatty substance present in a total amount ranging from 30% to 85% by weight relative to the total weight of the ready-to-use composition, at least one of the at least one fatty substance being chosen from fatty amides and fatty acid esters,
B) at least one dye precursor,
C) at least one oxidizing agent and optionally
D) at least one alkaline agent.

22. A multi-compartment kit, comprising
a first compartment which contains a composition comprising at least one fatty substance wherein at least one of the at least one fatty substance being chosen from fatty amides and fatty acid esters,
a second compartment comprising at least one dye precursor and optionally at least one alkaline agent, and
a third compartment comprising at least one oxidizing agent, and optionally at least one fatty substance.

23. A multi-compartment kit, comprising
a first compartment comprising at least one fatty substance wherein at least one of the at least one fatty substance being chosen from fatty amides and fatty acid esters and at least one oxidizing agent, and
a second compartment comprising at least one dye precursor and optionally at least one alkaline agent.

* * * * *